(12) United States Patent
Raul et al.

(10) Patent No.: US 7,939,570 B2
(45) Date of Patent: May 10, 2011

(54) CONTROLLED-RELEASE COMPOSITION FOR TOPICAL APPLICATION AND A METHOD OF DELIVERING AN ACTIVE AGENT TO A SUBSTRATE

(75) Inventors: Victor A. Raul, Midland, MI (US); Xavier Jean-Paul Thomas, Foix (FR); Anne K. Shim, Plaistow, NM (US); Gerald K. Schalau, II, Freeland, MI (US); Janelle L. Cabala, Beaverton, MI (US)

(73) Assignee: Dow Corning Corporation, Midland, MI (US)

( * ) Notice: Subject to any disclaimer, the term of this patent is extended or adjusted under 35 U.S.C. 154(b) by 942 days.

(21) Appl. No.: 10/576,991

(22) PCT Filed: Oct. 27, 2004

(86) PCT No.: PCT/US2004/035619
§ 371 (c)(1),
(2), (4) Date: Mar. 6, 2007

(87) PCT Pub. No.: WO2005/044232
PCT Pub. Date: May 19, 2005

(65) Prior Publication Data
US 2007/0244203 A1  Oct. 18, 2007

Related U.S. Application Data

(60) Provisional application No. 60/514,709, filed on Oct. 27, 2003.

(51) Int. Cl.
*A01N 25/00* (2006.01)
*A61K 47/00* (2006.01)
*A61Q 5/12* (2006.01)

(52) U.S. Cl. .................................. 514/770; 424/70.12
(58) Field of Classification Search ................ 514/770; 424/70.12
See application file for complete search history.

(56) References Cited

U.S. PATENT DOCUMENTS

| | | | |
|---|---|---|---|
| 2,676,182 A | 4/1954 | Daudt et al. | |
| 3,692,737 A | 9/1972 | Laur | |
| 4,152,416 A | 5/1979 | Spitzer et al. | |
| 4,310,678 A | 1/1982 | Blizzard et al. | |
| 4,423,095 A | 12/1983 | Blizzard | |
| 4,882,377 A | 11/1989 | Sweet et al. | |
| 4,885,129 A | 12/1989 | Leonard et al. | |
| 5,057,240 A | 10/1991 | Madore et al. | |
| 5,103,812 A | 4/1992 | Salamone et al. | |
| 5,178,881 A | 1/1993 | Mackles | |
| 5,356,585 A | 10/1994 | Romenesko | |
| RE35,474 E | 3/1997 | Woodard et al. | |
| 5,654,362 A | 8/1997 | Schulz, Jr. et al. | |
| 5,993,852 A | 11/1999 | Foldvari et al. | |
| 5,994,459 A | 11/1999 | Berg et al. | |
| 6,015,858 A | 1/2000 | Gornowicz | |
| 6,040,307 A * | 3/2000 | Gray et al. | 514/254.07 |
| 6,048,522 A | 4/2000 | Plochocka et al. | |
| 6,074,652 A | 6/2000 | Ishiwatari et al. | |
| 6,174,517 B1 | 1/2001 | Hansenne et al. | |
| 6,211,243 B1 | 4/2001 | Johnson | |
| 6,271,295 B1 | 8/2001 | Powell et al. | |
| 6,337,086 B1 | 1/2002 | Kanios et al. | |
| 6,365,146 B1 * | 4/2002 | Uhrich | 424/78.31 |
| 6,420,431 B1 | 7/2002 | Johnson | |
| 6,423,750 B1 | 7/2002 | Johnson | |
| 6,545,086 B1 * | 4/2003 | Kosal | 524/806 |
| 2001/0046507 A1 | 11/2001 | Dietz et al. | |
| 2003/0180281 A1 | 9/2003 | Bott et al. | |
| 2004/0105874 A1 | 6/2004 | Bott et al. | |
| 2005/0249791 A1 | 11/2005 | Hobbs et al. | |
| 2006/0135626 A1 | 6/2006 | Shim et al. | |

FOREIGN PATENT DOCUMENTS

| | | |
|---|---|---|
| EP | 0413418 A2 | 2/1991 |
| EP | 0846461 A1 | 6/1998 |
| JP | 6507172 | 8/1994 |
| JP | 8504759 | 5/1996 |
| JP | 9002929 A | 1/1997 |
| JP | 2001247452 A | 9/2001 |
| WO | 9218147 A1 | 10/1992 |
| WO | 9408604 A1 | 4/1994 |
| WO | 9744001 A1 | 11/1997 |
| WO | 99/11247 | 3/1999 |
| WO | 9911247 A1 | 3/1999 |
| WO | 03082356 A2 | 10/2003 |

(Continued)

OTHER PUBLICATIONS

U.S. Appl. No. 60/489,405, filed Jul. 23, 2003, Title: A Mechanical Inversion Process for Making Silicone Oil-In-Water Emulsions.

(Continued)

*Primary Examiner* — Shengjun Wang
*Assistant Examiner* — Sarah Pihonak
(74) *Attorney, Agent, or Firm* — Dinsmore & Shohl LLP

(57) ABSTRACT

A controlled-release composition for topical application to a substrate includes an oil-in-water emulsion and an active agent incorporated into the oil-in-water emulsion. The oil-in-water emulsion is substantially free of lipophilic solvent and is formed by mechanical inversion of a water-in-oil emulsion. The water-in-oil emulsion includes a silicone component, a surfactant, and water. A method of delivering the active agent to the substrate provides the oil-in-water emulsion and incorporates the active agent into the oil-in-water emulsion for delivery of the active agent to the substrate upon application of the oil-in-water emulsion to the substrate.

41 Claims, 3 Drawing Sheets

FOREIGN PATENT DOCUMENTS

| | | |
|---|---|---|
| WO | 03083031 A1 | 10/2003 |
| WO | WO03/086329 A2 | 10/2003 |
| WO | WO03/101404 A3 | 12/2003 |

OTHER PUBLICATIONS

Japanese Official Action (English translation of A Notification of Reason(s) for Refusal) dated Nov. 24, 2009 pertaining to Japanese Patent Application No. 2006-538212.

Chinese Office Action pertaining to Chinese Application No. 200480037305.4 dated Feb. 5, 2010.

Japanese Notice of Reasons for Rejection dated Mar. 16, 2010 pertaining to related Japanese Application No. 2006-538224.

Chinese Decision of Rejection dated Mar. 18, 2010 pertaining to related Chinese Application No. 200480031651.1.

Dow Corning Adhesives for Healthcare (2004) pp. 1-2.

* cited by examiner

CONTROLLED-RELEASE COMPOSITION FOR TOPICAL APPLICATION AND A METHOD OF DELIVERING AN ACTIVE AGENT TO A SUBSTRATE

RELATED APPLICATIONS

This application claims priority to and all the advantages of International Application No. PCT/US2004/035619, filed on Oct. 27, 2004, which claims priority to U.S. Provisional Patent Application No. 60/514,709, filed on Oct. 27, 2003.

BACKGROUND OF THE INVENTION

1. Field of the Invention

The subject invention generally relates to a controlled-released composition for topical application to a substrate. The subject invention also generally relates to a method of delivering an active agent to the substrate. More specifically, the controlled-release composition and method of this invention incorporate an active agent into an oil-in-water emulsion for delivery of the active agent to the substrate upon application of the oil-in-water emulsion to the substrate.

2. Description of the Related Art

Oil-in-water emulsions and their uses are known across many industries. As one example, oil-in-water emulsions have been used throughout the medical industry as mediums for the controlled release of active agents. These oil-in-water emulsions more specifically include a silicone component, such as a silicone-based pressure sensitive adhesive, a surfactant, and water. It is known that the silicone component is generally highly viscous and difficult to process along with the surfactant and water. More specifically, the silicone component has a high elastic modulus and viscous modulus. Such Theological properties provide a resistance to deform and make the silicone component difficult to process along with the surfactant and water. Due to the high viscosity and other Theological properties of the silicone component in the oil-in-water emulsion, the processes by which silicone-containing oil-in-water emulsion can be produced have typically been limited to emulsion polymerization.

Other processes for producing the oil-in-water emulsion are known and include mechanical processes such as mechanical emulsification and mechanical emulsification by inversion. However, the oil-in-water emulsion can only be produced by these mechanical processes if the emulsion incorporates a solvent or solvents to essentially reduce or 'cut' the viscosity of the silicone component in the emulsion. Use of additional solvents to reduce the viscosity is undesirable in most applications due to a variety of reasons, such as health, safety, and environmental concerns.

Due to the inherent difficulties associated with producing oil-in-water emulsions by the mechanical processes without additional solvent, active agents have not, to date, been strategically incorporated into an oil-in-water emulsion that is substantially free of the additional solvents and that is produced according to the mechanical emulsification by inversion process referenced above. Furthermore, it is known that the active agents are typically difficult to uniformly incorporate, i.e., disperse, into the oil-in-water emulsion without any agglomerates. As a result, such emulsions have not been utilized as controlled-release compositions for topical application to a substrate, such as the skin of a human or animal. Nor have such emulsions been used as an instrument to deliver the active agent to the substrate.

SUMMARY OF THE INVENTION AND ADVANTAGES

A controlled-release composition and a method are disclosed. The controlled-release composition is for topical application to a substrate and the method delivers an active agent to the substrate.

The composition includes an oil-in-water emulsion that is substantially free of lipophilic solvent and that is formed by mechanical inversion of a water-in-oil emulsion. The water-in-oil emulsion includes a silicone component, a surfactant, and water. The composition also includes the active agent which is dispersed in the oil-in-water emulsion.

The method provides the oil-in-water emulsion and incorporates the active agent into the oil-in-water emulsion. As such, the active agent can be delivered to the substrate upon application of the oil-in-water emulsion to the substrate.

Accordingly, the subject invention provides an oil-in-water emulsion that is substantially free of lipophilic solvents, that is produced according to the mechanical inversion of a water-in-oil emulsion, and that includes an active agent for delivery to a substrate in a controlled manner upon application to the substrate. Advantageously, the active agent and the surfactant can be added to the oil-in-water emulsion during various emulsification steps that are undertaken to provide the emulsion or after the oil-in-water emulsion has been provided in a post-add situation without effecting a drug release profile of the active agent or the overall stability of the oil-in-water emulsion.

DETAILED DESCRIPTION OF THE INVENTION

Figure 1:
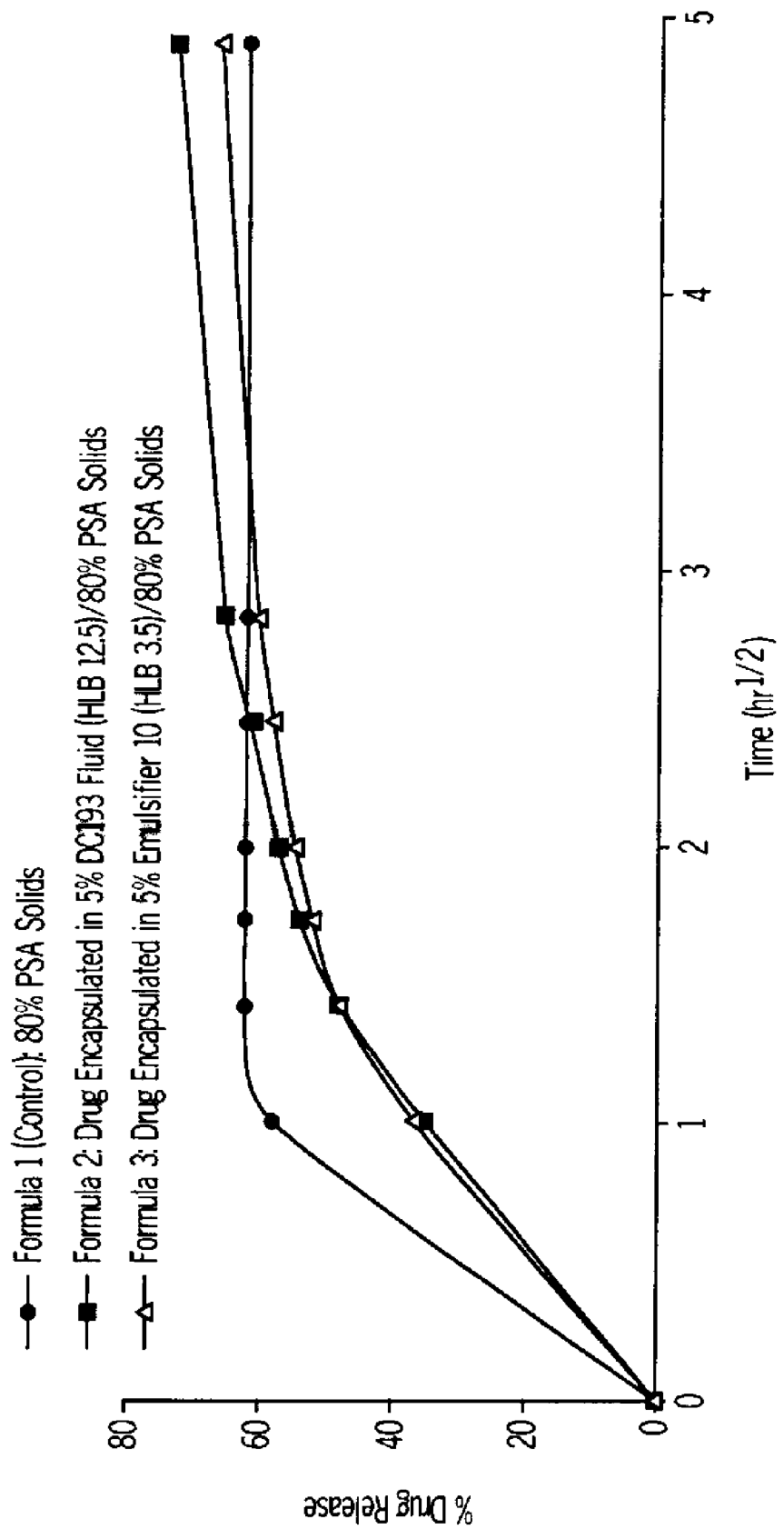
FIG. 1 is a graph showing the High Shear PSA O/W Emulsion: 24 hour 5% w/w Niacinamide.

The present invention includes a controlled-release composition, essentially an oil-in-water (O/W) emulsion that has been specifically processed and an active agent, for topical application to a substrate. The present invention also includes a method of delivering the active agent to the substrate. The substrate is typically a biological surface, human body tissue, and/or animal body tissue. More specific substrates include, but are not limited to, skin, hair, mucous membrane, tooth, nails, and eyes.

The present invention is typically applied for topical therapy, such as to treat damaged or diseased skin, and wound care, such as to treat cuts, burns, and the like, with a dressing formed from, or including, the controlled-release composition where the O/W emulsion primarily functions as a substantive cream or a liquid bandage that continuously delivers the active agent to the substrate. The present invention, including films formed by the controlled-release composition of the present invention, may also be applied in various transdermal, pharmaceutical, veterinary, and oral health care applications. It may be used as an in situ formed patch standing by itself, or it can be protected with a secondary film, dressing or patch, or it can be part of a more complex construction such as a transdermal patch or wound dressing. As alluded to above, the controlled-release composition, which is hereinafter simply referred to as the composition, includes the O/W emulsion and the active agent. The active agent is incorporated into the O/W emulsion.

The O/W emulsion is formed by mechanical inversion of a water-in-oil (W/O) emulsion as described additionally below, and the O/W emulsion is substantially free of lipophilic solvent. Mechanical inversion is also referred to in the art as mechanical inversion emulsification. The W/O emulsion, which is the basis for the O/W emulsion prior to mechanical inversion, includes a silicone component and a surfactant, preferably in a homogenous oil phase, and also includes water. If the active agent is in powder form or crystalline form, as described below, then the terminology "substantially free of lipophilic solvent" denotes that the O/W emulsion is free of lipophilic solvent but for any lipophilic solvents present as a result of the silicone component. On the other hand, it the active agent is in liquid or viscous form, as described below, then the terminology "substantially free of lipophilic solvent" denotes that the O/W emulsion is free of lipophilic solvent but for any lipophilic solvents present as a result of the silicone component or as a result of any solvents in the active agent. Mechanical inversion of the W/O emulsion provides an effective process for emulsifying the silicone component without use of supplemental solvents to reduce the high viscosity of the silicone component. The O/W emulsion resulting from this process is stable over time.

The silicone component of the O/W emulsion, which is present in the W/O emulsion, is any silicone-containing polymer material (e.g. wax, gum, resin, elastomer base, sealant, adhesive, etc.). Preferably, the silicone component is a pressure sensitive adhesive (PSA). More preferably, the silicone component is a PSA that is the reaction product of a hydroxy endblocked polydimethylsiloxane polymer and a hydroxy functional silicate resin. Preferably, the hydroxy functional silicate resin is a trimethylsiloxy and hydroxy endblocked silicate resin. The polymer and resin react in a condensation reaction to form the PSA. Although the PSA is most preferred, other forms of the silicone component include a silicone gum, a silicone rubber, a silicone elastomer, a silicone resin, high molecular weight silicones, or mixtures thereof these components. These other forms of the silicone component are possible because they form a film. However, these other forms are not necessarily preferred because they lack substantivity as compared to the PSA. Along with the active agent, the PSA functions as a bio-adhesive. The advantage of using the PSA as the silicone component is the substantivity that the PSA provides. This substantivity is particularly advantageous in human and veterinary applications that require significant substantivity for the active agent to provide sustained pharmacological affects.

The silicone components that are emulsified according to the mechanical inversion process, specifically the PSA, the silicone gum, the silicone rubber, the silicone elastomer, the silicone resin, and the high molecular weight silicones, have viscosities of at least 100,000,000 (100 million) centistoke (mm$^2$/s) to 5,000,000,000 (5 billion) centistoke (mm$^2$/s), preferably of at least 200,000,000 (200 million) centistoke (mm$^2$/s) to 2,000,000,000 (2 billion) centistoke (mm$^2$/s), and most preferably of at least 1,000,000,000 (1 billion) centistoke (mm$^2$/s).

For purposes of this invention, the terms silicone rubber and silicone elastomer are synonymous, at least to the extent that both silicone components are capable of elongation and recovery. In contrast, silicone gums are capable of being stretched, but they do not generally snap back. Silicone gums are the high molecular weight, generally linear, polydiorganosiloxanes that can be converted from their highly viscous plastic state into a predominately elastic state by crosslinking. Silicone gums are often used as one of the main components in the preparation of silicone rubbers and silicone elastomers.

For purposes of this invention therefore, silicone gum can be considered to include compositions of the type described in U.S. Pat. No. 3,692,737 (issued Sep. 19, 1972); U.S. Pat. No. 4,152,416 (issued May 1, 1979), U.S. Pat. No. 4,885,129 (issued Aug. 8, 1989), and U.S. Pat. No. 5,057,240 (issued Oct. 15, 1991), the disclosures of which are hereby incorporated by reference in their entirety.

Silicone rubbers and silicone elastomers can be considered to include compositions of the type described in U.S. Pat. No. 4,882,377 (issued Nov. 21, 1989), U.S. Pat. No. 5,654,362 (issued Aug. 5, 1997), U.S. Pat. No. 5,994,459 (issued Nov. 30, 1999), and U.S. Pat. No. 6,015,858 (issued Jan. 18, 2004), the disclosures of which are hereby incorporated by reference in their entirety.

Silicone resins can be considered to include compositions of the type described in U.S. Pat. No. 2,676,182 (issued Apr. 20, 1954), U.S. Pat. No. 4,310,678 (issued Jan. 12, 1982), U.S. Pat. No. 4,423,095 (issued Dec. 27, 1983), and U.S. Pat. No. 5,356,585 (issued Oct. 18, 1994), the disclosures of which are hereby incorporated by reference in their entirety.

The silicone resins of the subject invention may also be considered to include MQ resins. The acronym MQ as it relates to silicone resins is derived from the symbols M, D, T, and Q each of which represent a functionality of different types of structural units which may be present in silicone resins containing siloxane units joined by $\equiv$Si—O—Si$\equiv$ bonds. The monofunctional (M) unit represents $(CH_3)_3SiO_{1/2}$ and the difunctional (D) unit represents $(CH_3)_2SiO_{2/2}$. The trifunctional (T) unit represents $CH_3SiO_{3/2}$ and results in the formation of branched linear siloxanes. The tetrafunctional (Q) unit represents $SiO_{4/2}$ which results in the formation of crosslinked and resinous silicone compositions. Hence, MQ is used when the siloxane contains all monofunctional M and tetrafunctional Q units, or at least a high percentage of M and Q units such as to render the silicone resinous.

Silicone resins useful herein are non-linear siloxane resins having a glass transition temperature (Tg) above 0° C. Glass transition temperature is the temperature at which an amorphous material such as a higher silicone polymer changes from a brittle vitreous state to a plastic state. Thin silicone resin generally has the formula $R'_aSiO_{(4-a)/2}$ wherein R' is a monovalent hydrocarbon group with 1-6 carbon atoms or a functionally substituted hydrocarbon group with 1-6 carbon atoms, and a has an average value of 1-1.8. The silicone resin will preferably include monofunctional (M) units $R''_3SiO_{1/2}$ and tetrafunctional (Q) units $SiO_{4/2}$, in which R'' is the monovalent hydrocarbon group having 1-6 carbon atoms, most preferably the methyl group. Typically, the number ratio of M groups to Q groups will be in the range of 0.5:1 to 1.2:1, so as to provide an equivalent wherein a in the formula $R'_aSiO_{(4-a)/2}$ has an average value of 1.0-1.63. Preferably, the number ratio is 0.6:1 to 0.9:1. Most preferred are silicone MQ resins in which the number of Q units per molecule is higher than 1, preferably higher than 5.

The silicone resin may also contain 1-5 percent by weight of silicon-bonded hydroxyl radicals such as a dimethylhydroxysiloxy unit $(HO)(CH3)_2SiO_{1/2}$. If desired, the silicone resin may contain minor amounts of difunctional (D) units and/or trifunctional (T) units. Preferred silicone resins are those having a viscosity of at least 100,000,000 (100 million) centistoke (mm$^2$/s) and a softening temperature of less than about 200° C. The silicone resin may include (i) silicone resins of the type $M_xQ_y$ where x and y have values such that the silicone resin contains at least more than 5 Q units per molecule; (ii) silicone resins of the type $M_xT_y$ where x and y have values such that the silicone resin contains at least more than 5 T units per molecule; and (iii) silicone resins of the type $M_xD_yT_pQ_q$ where x, y, p, and q have values such that the sum of Q and T units is at least more than 5 units per molecule, and the number of D units varies from 0-100.

As set forth above, the O/W emulsion includes a surfactant. The surfactant may be an anionic surfactant, cationic surfactant, nonionic surfactant, amphoteric surfactant, or a mixture of these surfactants. Nonionic surfactants and anionic surfactants are preferred, and most preferred are mixtures containing an anionic and a nonionic surfactant, or a mixtures containing two nonionic surfactants. When mixtures containing nonionic surfactants are used, one nonionic surfactant should have a low hydrophilic-lipophilic balance (HLB) and the other nonionic surfactant should have a high HLB, such that the two nonionic surfactants have a combined HLB of 11-15, preferably a combined HLB of 12.5-14.5.

Representative examples of suitable anionic surfactants include alkali metal soaps of higher fatty acids, alkylaryl sulphonates such as sodium dodecyl benzene sulphonate, long chain fatty alcohol sulphates, olefin sulphates and olefin sulphonates, sulphated monoglycerides, sulphated esters, sulphonated ethoxylated alcohols, sulphosuccinates, alkane sulphonates, phosphate esters, alkyl isethionates, alkyl taurates, and alkyl sarcosinates. One example of a preferred anionic surfactant is sold commercially under the name Bio-Soft N-300. It is a triethanolamine linear alkylate sulphonate composition marketed by the Stephan Company, Northfield, Ill.

Representative examples of suitable cationic surfactants include alkylamine salts, quaternary ammonium salts, sulphonium salts, and phosphonium salts. Representative examples of suitable nonionic surfactants include condensates of ethylene oxide with long chain fatty alcohol or fatty acids such as a $C_{12-16}$ alcohol, condensates of ethylene oxide with an amine or an amide, condensation products of ethylene and propylene oxide, esters of glycerol, sucrose, sorbitol, fatty acid alkylol amides, sucrose esters, fluoro-surfactants, and fatty amine oxides. Representative examples of suitable amphoteric surfactants include imidazoline compounds, alkylaminoacid salts, and betaines.

Representative examples of suitable commercially available nonionic surfactants include polyoxyethylene fatty alcohols sold under the tradename BRIJ by Uniqema (ICI Surfactants), Wilmington, Del. Some examples are BRIJ 35 Liquid, an ethoxylated alcohol known as polyoxyethylene (23) lauryl ether, and BRIJ 30, another ethoxylated alcohol known as polyoxyethylene (4) lauryl ether. Some additional nonionic surfactants include ethoxylated alcohols sold under the trademark TERGITOL® by The Dow Chemical Company, Midland, Mich. Some example are TERGITOL® TMN-6, an ethoxylated alcohol known as ethoxylated trimethylnonanol; and various of the ethoxylated alcohols, i.e., $C_{12}$-$C_{14}$ secondary alcohol ethoxylates, sold under the trademarks TERGITOL® 15-S-5, TERGITOL® 15-S-12, TERGITOL® 15-S-15, and TERGITOL® 15-S-40. Surfactants containing silicon atoms can also be used.

Upon the providing of the O/W emulsion, which includes the silicone component, the surfactant, and the water, the active agent is incorporated, or dispersed, into the O/W emulsion for delivery of the active agent to the substrate upon application of the O/W emulsion to the substrate. The terminology "active agent" denotes any substance, with the exception of enzymes, that is able to produce an effect, whether physical, chemical, or biological. Although the active agent may be in liquid or viscous form, it is typically in powder form or crystalline form. The active agent can be post-added into the O/W emulsion whether or not it is combined with a dispersing agent and/or encapsulated by the dispersing agent as described below. Alternatively, the active agent can be incorporated during the steps to provide the O/W emulsion.

The active agent may include a lipophilic drug and/or hydrophilic drug with the exception of natural, synthetic, or engineered enzymes. One example of a lipophilic drug that is suitable for incorporation into the O/W emulsion is ketoconazole. Examples of the hydrophilic drug that are suitable for incorporation into the O/W emulsion are niacinamide and hydrogen peroxide. Whether or not the active agent is a lipophilic drug or a hydrophilic drug, other possible active agents include, but are not limited to, antiacne agents, such as salicylic acid and sulfur, antibiotic, antiseptic, antifungal agents, such as calcium undecylenate, undecylenic acid, zinc undecylenate, and povidone-iodine, antibacterial, antimicrobial agents, such as alcohol, benzalkonium chloride, benzethonium chloride, hydrogen peroxide, methylbenzethonium chloride, phenol, poloxamer 188, silver ions, nanocrystalline silver, biocides, antiinflammatory, astringents, anticancer agents, smoking cessation compositions, cardiovascular, histamine blocker, bronchodilator, analgesic, antiarrythmic, antihistamine, alpha-I blocker, beta blocker, ACE inhibitor, diuretic, antiaggregant, sedative, tranquilizer, anticonvulsant, anticoagulant agents, vitamins, antiaging agents, agents for treating gastric and duodenal ulcers, anticellulites, cell growth nutrients, perfumes, UV protectors, shaving products, deodorants, therapeutic active agents such as penicillins, cephalosporins, tetracyclines, macrolides, epinephrine, amphetamines, aspirin, acetominophen, barbiturates, catecholamines, benzodiazepine, thiopental, codeine, morphine, procaine, lidocaine, lidocaine HCL, benzocaine, sulphonamides, ticonazole, perbuterol, furosamide, prazosin, prostaglandins, salbutamol, indomethicane, diclofenac, glafenine, dipyridamole, theophylline and retinol, drugs that act upon the central nervous system (such as clozapine, risperidone, chordiazepoxide, buspirone, desipramine, maprotiline, amitriptyline, timolol, selegiline, naloxone and nalbuphine), drugs affecting renal and cardiovascular function (such as acetazolamide, isosorbide, furosemide, chlorothiazide, amiloride, captopril, enalapril, lisinopril, isosorbide nitrate, nifedipine, verapamil, phenytoin, lidocaine, propranolol, amiodarone, pravastatin, probucol and ciprofibrate), drugs affecting gastrointestinal function (such as cimetidine, omeprazole and ranitidine), drugs for the treatment of helminthiasis (such as thiabendazole and mebendazole), drugs for the treatment of microbial diseases (such as trimethoprim, norfloxacin, ciprofloxacin, penicillin G nafcillin, cephalothin cefazolin, kanamycin A, neomycin, doxycycline minocycline, clarithromycin, clindamycin, flucytosine, ketoconazole, fluconazole, acyclovir and ganciclovir), drugs for the treatment of neoplastic diseases (such as dacarbazine, busulfan, and triazenes), drugs for the treatment of nutrient deficiency (such as folic acid, niacinamide, ascorbic acid and thiamine), drugs for hormonal replacement therapy (such as estradiol, ethinyl estradiol and norethindrone), drugs that inhibit the synthesis and actions of adrenocortical hormones (such as cortisol, cortisone and prednisone), and drugs used in dermatology for the treatment of dermatoses (such as betamethasone dipropionate, hydrocortisone, dexamethasone sodium phosphate, retinal, tretinoin, isotretinoin, dapsone, calipotriene, ketoconazole, clotrimazole, itraconazole and arotinoid).

It is preferred that the active agent is combined with the dispersing agent to form a dispersion prior to incorporation of the active agent into the O/W emulsion. The combination is generally in a 1:1 ratio by weight of the active agent and the dispersing agent. If the active agent is combined with the dispersing agent, it is possible that the two components are combined by simple mixing or combined in a mortar and dispersed together with a pestle. The dispersing agent disperses the active agent and further functions to reduce and/or eliminate any agglomerates of the active agent which, as described above, is typically in powder or crystalline form. Once this dispersion is formed, the dispersion, which includes the active agent, is then incorporated into the O/W emulsion. Even further, in the most preferred embodiment, the active agent is at least partially, if not entirely, encapsulated in the dispersing agent prior to incorporation of the active agent into the O/W emulsion.

Although not required, it is preferred that the dispersing agent is a surfactant. If a surfactant, the dispersing agent can be the same as or different from the surfactant utilized in providing the O/W emulsion. The dispersing agent allows a controlled rate of the delivery of the active agent to the substrate. Most preferably, the dispersing agent is a silicone-based surfactant. Other possibilities for the dispersing agent include, but are not limited to, nonionic surfactants (such as polyols, polyethylene glycols, Pluronic® Surfactants, Plurafac® Surfactants, MYRJ® Surfactants, SPAN® Surfactants, BRIJ® Surfactants, TWEEN® Surfactants, Triton® Surfactants, and Polyox® Surfactants, and the like), anionic surfactants (such as sodium lauryl sulfate, dioctylesodium-sulfosuccinate, and the like), ethers (such as the glycol ethers), low molecular weight esters (such as triethyl citrate, diacetin and dioctyl adipate), and low molecular weight glycols (such as propylene glycol and diethylene glycol).

As alluded to above, the dispersing agent functions to control the rate of the delivery of the active agent to the substrate. That is, the dispersing agent functions as a drug release modulator to control the rate at which the active agent is released for delivery to the substrate.

In addition to the active agent and the dispersing agent, various excipients may be incorporated into the O/W emulsion. As generally understood by those skilled in the art, excipients are additives that are used to convert the active agent into appropriate dosage forms that are suitable for application to the substrate. Excipients may also be added to stabilize the O/W emulsion and to optimize application characteristics, such as flowability. Examples of potential excipients include, but are not limited to, those that are found in the CTFA ingredient Database and the handbook of pharmaceutical excipients such as absorbents, anticacking agents, antioxidants (such as acetyl cysteine, arbutin, ascorbic acid, ascorbic acid polypeptide, ascorbyl dipalmitate, ascorbyl methylsilanol pectinate, ascorbyl palmitate, ascorbyl stearate, BHA, p-ydroxyanisole, BHT, t-butyl hydroquinone, caffeic acid, camellia sinensis oil, chitosan ascorbate, chitosan glycolate, chitosan salicylate, chlorogenic acids, cysteine, cysteine HCI, decyl mercaptomethylimidazole, erythorbic acid, diamylhydroquinone, di-t-butylhydroquinone, dicetyl thiodipropionate, dicyclopentadiene/t-butylcresol copolymer, digalloyl trioleate, dilauryl thiodipropionate, dimyristyl thiodipropionate, dioleyl tocopheryl methylsilanol, isoquercitrin, diosmine, disodium ascorbyl sulfate, disodium rutinyl disulfate, distearyl thiodipropionate, ditridecyl thiodipropionate, dodecyl gallate, ethyl ferulate, ferulic acid, hydroquinone, hydroxylamine HCI, hydroxylamine sulfate, isooctyl thioglycolate, kojic acid, madecassicoside, magnesium ascorbate, magnesium ascorbyl phosphate, melatonin, methoxy-PEG-7 rutinyl succinate, methylene di-t-butylcresol, methylsilanol ascorbate, nordihydroguaiaretic acid, octyl gallate, phenylthioglycolic acid, phloroglucinol, potassium ascorbyl tocopheryl phosphate, thiodiglycolamide, potassium sulfite, propyl gallate, rosmarinic acid, rutin, sodium ascorbate, sodium ascorbyl/cholesteryl phosphate, sodium bisulfite, sodium erythorbate, sodium metabisulfide, sodium sulfite, sodium thioglycolate, sorbityl furfural, tea tree (melaleuca aftemifolia) oil, tocopheryl acetate, tetrahexyldecyl ascorbate, tetrahydrodiferuloylmethane, tocopheryl linoleate/oleate, thiodiglycol, tocopheryl succinate, thiodiglycolic acid, thioglycolic acid, thiolactic acid, thiosalicylic acid, thiotaurine, retinol, tocophereth-5, tocophereth-10, tocophereth-12, tocophereth-18, tocophereth-50, tocopherol, tocophersolan, tocopheryl linoleate, tocopheryl nicotinate, tocoquinone, o-tolyl biguanide, tris(nonylphenyl) phosphite, ubiquinone, and zinc dibutyldithiocarbamate), antistatic agents, astringents, binders, buffering agents, bulking agents, chelating agents, colorants, cosmetic astringents, cosmetic biocides (such as aluminum phenolsulfonate, Ammonium Phenolsulfonate, Bakuchiol, Benzalkonium Bromide, Benzalkonium Cetyl Phosphate, Benzalkonium Chloride, Benzalkonium Saccharinate, Benzethonium Chloride, Potassium Phenoxide, Benzoxiquine, Benzoxonium Chloride, Bispyrithione, Boric Acid, Bromochlorophene, Camphor Benzalkonium Methosulfate, Captan, Cetalkonium Chloride, Cetearalkonium Bromide, Cetethyldimonium Bromide, Cetrimonium Bromide, Cetrimonium Chloride, Cetrimonium Methosulfate, Cetrimonium Saccharinate, Cetrimonium Tosylate, Cetylpyridinium Chloride, Chloramine T, Chlorhexidine, Chlorhexidine Diacetate, Chlorhexidine Digluconate, Chlorhexidine Dihydrochloride, p-Chloro-m-Cresol, Chlorophene, p-Chlorophenol, Chlorothymol, Chloroxylenol, Chlorphenesin, Ciclopirox Olamine, Climbazole, Cloflucarban, Clotrimazole, Coal Tar, Colloidal Sulfur, o-Cymen-5-ol, Dequalinium Acetate, Dequalinium Chloride, Dibromopropamidine Diisethionate, Dichlorobenzyl Alcohol, Dichlorophene, Dichlorophenyl Imidazoldioxolan, Dichloro-m-Xylenol, Diiodomethyltolylsulfone, Dimethylol Ethylene Thiourea, Diphenylmethyl Piperazinylbenzimidazole, Domiphen Bromide, 7-Ethylbicyclooxazolidine, Fluorosalan, Formaldehyde, Glutaral, Hexachlorophene, Hexamidine, Hexamidine Diisethionate, Hexamidine Diparaben, Hexamidine Paraben, Hexetidine, Hydrogen Peroxide, Hydroxymethyl Dioxoazabicyclooctane, Ichthammol, Isopropyl Cresol, Lapyrium Chloride, Lauralkonium Bromide, Lauralkonium Chloride, Laurtrimonium Bromide, Laurtrimonium Chloride, Laurtrimonium Trichlorophenoxide, Lauryl Isoquinolinium Bromide, Lauryl Isoquinolinium Saccharinate, Laurylpyridinium Chloride, Mercuric Oxide, Methenamine, Methenammonium Chloride, Methylbenzethonium Chloride, Myristalkonium Chloride, Myristalkonium Saccharinate, Myrtrimonium Bromide, Nonoxynol-9 Iodine, Nonoxynol-12 Iodine, Olealkonium Chloride, Oxyquinoline, Oxyquinoline Benzoate, Oxyquinoline Sulfate, PEG-2 Coco-Benzonium Chloride, PEG-10 Coco-Benzonium Chloride, PEG-6 Undecylenate, PEG-8 Undecylenate, Phenol, o-Phenylphenol, Phenyl Salicylate, Piroctone Olamine, Sulfosuccinylundecylenate, Potassium o-Phenylphenate, Potassium Salicylate, Potassium Troclosene, Propionic Acid, PVP-Iodine, Quaternium-8, Quaternium-14, Quaternium-24, Sodium Phenolsulfonate, Sodium Phenoxide, Sodium o-Phenylphenate, Sodium Shale Oil Sulfonate, Sodium Usnate, Thiabendazole, 2,2'-Thiobis(4-Chlorophenol), Thiram, Triacetin, Triclocarban, Triclosan, Trioctyldodecyl Borate, Undecylenamidopropylamine Oxide, Undecyleneth-6, Undecylenic Acid, Zinc Acetate, Zinc Aspartate, Zinc Borate, Zinc Chloride, Zinc Citrate, Zinc Cysteinate, Zinc Dibutyldithiocarbamate, Zinc Gluconate, Zinc Glutamate, Zinc Lactate, Zinc Phenolsulfonate, Zinc Pyrithione, Zinc Sulfate, and Zinc Undecylenate), deodorant agents, emollients, external analgesics (such as Benzyl Alcohol, Capsicum Oleoresin (Capsicum Frutescens Oleoresin), Methyl Salicylate, Camphor, Phenol, Capsaicin, Juniper Tar (Juniperus Oxycedrus Tar), Phenolate Sodium (Sodium Phenoxide), Capsicum (Capsicum Frutescens), Menthol, Resorcinol, Methyl Nicotinate, and Turpentine Oil (Turpentine)), film formers, flavoring agents, fragrance ingredients, humectants, lytic agents, moisturizing agents, occlusivity enhancers, opacifying agents, oxidizing agents (such as Ammonium Persulfate, Calcium Peroxide, Hydrogen Peroxide, Magnesium Peroxide, Melamine Peroxide, Potassium Bromate, Potassium Caroate, Potassium Chlorate, Potassium Persulfate, Sodium Bromate, Sodium Carbonate Peroxide, Sodium Chlorate, Sodium Iodate, Sodium Perborate, Sodium Persulfate, Strontium Dioxide, Strontium Peroxide, Urea Peroxide, and Zinc Peroxide), reducing agents (such as Ammonium Bisufite, Ammonium Sulfite, Ammonium Thioglycolate, Ammonium Thiolactate, Cystemaine HCl, Cystein, Cysteine HCl, Ethanolamine Thioglycolate, Glutathione, Glyceryl Thioglycolate, Glyceryl Thiopropionate, Hydroquinone, p-Hydroxyanisole, Isooctyl Thioglycolate, Magnesium Thioglycolate, Mercaptopropionic Acid, Potassium Metabisulfite, Potassium Sulfite, Potassium Thioglycolate, Sodium Bisulfite, Sodium Hydrosulfite, Sodium Hydroxymethane Sulfonate, Sodium Metabisulfite, Sodium Sulfite, Sodium Thioglycolate, Strontium Thioglycolate, Superoxide Dismutase, Thioglycerin, Thioglycolic Acid, Thiolactic Acid, Thiosalicylic Acid, and Zinc Formaldehyde Sulfoxylate), penetration enhancers, pesticides, plasticizers, preservatives, skin bleaching agents such as hydroquinone, skin conditioning agents, skin protectants (such as Allantoin, Aluminum Acetate, Aluminum Hydroxide, Aluminum Sulfate, Calamine, Cocoa Butter, Cod Liver Oil, Colloidal Oatmeal, Dimethicone, Glycerin, Kaolin, Lanolin, Mineral Oil, Petrolatum, Shark Liver Oil, Sodium Bicarbonate, Talc, Witch Hazel, Zinc Acetate, Zinc Carbonate, and Zinc Oxide), slip modifiers, solubilizing agents, solvents, sunscreen agents (such as Aminobenzoic Acid, Cinoxate, Diethanolamine Methoxycinnamate, Digalloyl Trioleate, Dioxybenzone, Ethyl 4-[bis(Hydroxypropyl)]Aminobenzoate, Glyceryl Aminobenzoate, Homosalate, Lawsone with Dihydroxyacetone, Menthyl Anthranilate, Octocrylene, Octyl Methoxycinnamate, Octyl Salicylate, Oxybenzone, Padimate O, Phenylbenzimidazole Sulfonic Acid, Red Petrolatum, Sulisobenzone, Titanium Dioxide, and Trolamine Salicylate), surface modifiers, surfactants and emulsifying agents, suspending agents, thickening agents, viscosity controlling agents including increasing or decreasing agents, UV light absorbing agent (such as Acetaminosalol, Allatoin PABA, Benzalphthalide, Benzophenone, Benzophenone 1-12, 3-Benzylidene Camphor, Benzylidenecamphor Hydrolyzed Collagen Sulfonamide, Benzylidene Camphor Sulfonic Acid, Benzyl Salicylate, Bornelone, Bumetriozole, Butyl Methoxydibenzoylmethane, Butyl PABA, Ceria/Silica, Ceria/Silica Talc, Cinoxate, DEA-Methoxycinnamate, Dibenzoxazol Naphthalene, Di-t-Butyl Hydroxybenzylidene Camphor, Digalloyl Trioleate, Diisopropyl Methyl Cinnamate, Dimethyl PABA Ethyl Cetearyldimonium Tosylate, Dioctyl Butamido Triazone, Diphenyl Carbomethoxy Acetoxy Naphthopyran, Disodium Bisethylphenyl Tiamminotriazine Stilbenedisulfonate, Disodium Distyrylbiphenyl Triaminotriazine Stilbenedisulfonate, Disodium Distyrylbiphenyl Disulfonate, Drometrizole, Drometrizole Trisiloxane, Ethyl Dihydroxypropyl PABA, Ethyl Diisopropylcinnamate, Ethyl Methoxycinnamate, Ethyl PABA, Ethyl Urocanate, Etrocrylene Ferulic Acid, Glyceryl Octanoate Dimethoxycinnamate, Glyceryl PABA, Glycol Salicylate, Homosalate, Isoamyl p-Methoxycinnamate, Isopropylbenzyl Salicylate, Isopropyl Dibenzolylmethane, Isopropyl Methoxycinnamate, Menthyl Anthranilate, Menthyl Salicylate, 4-Methylbenzylidene, Camphor, Octocrylene, Octrizole, Octyl Dimethyl PABA, Octyl Methoxycinnamate, Octyl Salicylate, Octyl Triazone, PABA, PEG-25 PABA, Pentyl Dimethyl PABA, Phenylbenzimidazole Sulfonic Acid, Polyacrylamidomethyl Benzylidene Camphor, Potassium Methoxycinnamate, Potassium Phenylbenzimidazole Sulfonate, Red Petrolatum, Sodium Phenylbenzimidazole Sulfonate, Sodium Urocanate, TEA-Phenylbenzimidazole Sulfonate, TEA-Salicylate, Terephthalylidene Dicamphor Sulfonic Acid, Titanium Dioxide, TriPABA Panthenol, Urocanic Acid, and VA/Crotonates/Methacryloxybenzophenone-1 Copolymer). Other possible excipients include, but are not limited to, sugars and derivatives (such as acacia, dextrin, dextrose, fructose, lactose, maltodextrin, mannitol, sorbitol, sucrose, and xylitol), starch derivatives, cellulosic materials (such as Na Carboxymethylcellulose, Microcrystaline Cellulose, Cellulose Acetate Phtalate, Na croscarmellose, methyl cellulose, Ethylcellulose, Hydroxyethylcellulose, Hydroxypropylcellulose, Hydroxypropylmethylcellulose, and Hydroxypropylmethyl cellulose phtalate), polysaccharides (such as dextrates, guar gum, and xanthan gum), polyether (such as poloxamer, and polyoxyethylene alkyl ethers), polyvinyl alcohols, acrylic and methacrylic acid polymers (such as Carbomer, Polacrilin potassium, and polymethacrylates), pyrrolidone derivatives (such as povidone, and crospovidone), glycuronam polymer and derivatives (such as alginic acid, alginate salts (Ca, Na)), solid diluents (such as salts of carbonate (Ca, Mg), Ca Phosphate derivatives, Ca Sulfate, Mg oxide, Potassium Chloride, Potassium citrate), solid lubricants (such as stearate derivatives (Ca, Mg), talc, zinc oxide), suspending agents (such as kaolin, Mg Al silicate, and carbon), cyclodextrins, and others (including Cholesterol, Fumaric acid, lecithin, gelatin, malic acid, Na bicarbonate, Na citrate salts, Na stearyl fumarate, Ti dioxide, and Zinc oxide).

As indicated above, one type of excipient is a thickening agent. Thickening agents are typically added to stabilize the active agent and the O/W emulsion. Although not required, the thickening agent may encapsulate the active agent. If included, illustrative thickening agents include, but are not limited to, at least one of polyacrylic acids, cellulose derivatives, polyvinyl alcohol, polyvinylpyrrolidone, polysaccharides, acrylamide copolymers, biological polymers and derivatives, butylene copolymers, carbohydrates, carbomers, hydrophilic colloids and derivatives including salts and gums, polyacrylates and acrylate copolymers, synthetic polymers including salts, silica, calcium carbonates which can be untreated or treated with stearate or stearic acid, reinforcing silicas such as fumed silicas, precipitated silicas, and hydrophobed silicas, crushed quartz, ground quartz, alumina, aluminum hydroxide, titanium dioxide, diatomaceous earth, iron oxide, carbon black, and graphite, and resinous materials including silicone and organics.

Also, various cosmetic, personal care, and cosmeceutical components may be included aside from the excipient or excipients. Examples of suitable cosmetic, personal care, and cosmeceutical components include, but are not limited to, alcohols, fatty alcohols and polyols, aldehydes, alkanolamines, alkoxylated alcohols (e.g. polyethylene glygol derivatives of alcohols and fatty alcohols), alkoxylated amides, alkoxylated amines, alkoxylated carboxylic acids, amides including salts (e.g. ceramides), amines, amino acids including salts and alkyl substituted derivatives, esters, alkyl substituted and acyl derivatives, polyacrylic acids, acrylamide copolymers, adipic acid copolymers, alcohols, aminosilicones, butylene copolymers, carbohydrates (e.g. polysaccharides, chitosan and derivatives), carboxylic acids, carbomers, esters, ethers and polymeric ethers (e.g. PEG derivatives, PPG derivatives), glyceryl esters and derivatives, halogen compounds, heterocyclic compounds including salts, hydrophilic colloids and derivatives including salts and gums (e.g. cellulose derivatives, gelatin, xanthan gum, natural gums), imidazolines, inorganic materials (clay, TiO2, ZnO), ketones (e.g. camphor), isethionates, lanolin and derivatives, organic salts, phenols including salts (e.g. parabens), phosphorus compounds (e.g. phosphate derivatives), polyacrylates and acrylate copolymers, synthetic polymers including salts, siloxanes and silanes, sorbitan derivatives, sterols, sulfonic acids and derivatives and waxes.

The method of the subject invention includes more specific steps in order to provide the O/W emulsion. A homogeneous oil phase containing the silicone-component is formed. The silicone component in the homogenous oil phase has a viscosity of at least 100,000,000 (100 million) centistoke ($mm^2/s$) to 5,000,000,000 (5 billion) centistoke ($mm^2/s$). Next, the surfactant is mixed with the homogenous oil phase. As described above, more than one surfactant may be utilized in providing the O/W emulsion. Water is then added to the homogeneous oil phase to form the W/O emulsion containing a continuous phase and a dispersed phase. Preferably, the water is added in an amount of about 0.5-10, more preferably of about 1-5, percent by weight based on the weight of the silicone component in the homogenous oil phase. While the water can be added in multiple portions, such as 2-4 portions, the addition of the water in a single portion is preferred. In an alternative embodiment, rather than separately mixing the surfactant with the homogenous oil phase, the surfactant can be added along with the addition of the water.

Next, the W/O emulsion is mechanically-inverted into the O/W emulsion. This mechanical inversion is preferably accomplished by applying a high shear to the W/O emulsion in a twin-screw extruder having a length to diameter ratio (L/D) of at least 15. More preferably, the twin-screw extruder has a L/D of at least 30, and in the most preferred embodiment, the L/D is from 30 to 60. Many different types of twin-screw extruders are known in the art and are suitable for accomplishing the mechanical inversion. For example, the twin-screw extruder may be counter-rotating or co-rotating. It may be equipped with conical twin screws or parallel twin screws. The barrels of the twin-screw extruder may be divided into a number of zones and equipped with metering equipment for introducing materials along the length of the barrel. In the twin-screw extruder, the high shear is accomplished by mixing and agitating. The application of high shear in the twin-screw extruder causes inversion of the W/O emulsion into the O/W emulsion. Importantly, the O/W emulsion is provided by carrying out the mechanical inversion in the absence of any solvent other than solvents that are present in the silicone component, or in the silicone component and the active agent if the active agent is in liquid or viscous form. In alternative embodiments, the mechanical inversion may be accomplished by applying high shear to the W/O emulsion using a kneader extruder having a double-arm mixer with an extrusion screw, provided the kneader extruder is capable of functioning with the same efficiency as the twin-screw extruder.

Inversions generally occur when the continuous phase of a dispersion becomes the dispersed phase, or vice versa. Phase inversions in liquid/liquid dispersions are categorized as either catastrophic inversions or transitional inversions. Catastrophic inversions are caused by simply changing the phase ratio until there is a high enough ratio of the dispersed phase that it becomes the continuous phase. Transitional inversions occur when the affinity of the surfactant for the two phases is altered in order to cause the inversion. The inversions occurring in this invention are catastrophic inversions.

After inversion, the O/W emulsion may then be diluted with additional water. If added, the additional water is typically added after a desired particle size for the silicone component has been reached. The particle size of the silicone component in the O/W emulsion typically ranges from about 0.1 to 25.0 microns, with the mean particle size about 0.37 microns. Of course, the particle size varies depending on the amount and characteristics, i.e., type, of both the surfactant and the silicone component.

The dilution of the emulsion serves to achieve a preferred solids content for the O/W emulsion which is from 25 to 85 parts by weight based on 100 parts by weight of the O/W emulsion. This solids content may be selectively varied to achieve a target viscosity for ideal application of the O/W emulsion to the substrate or to control a rate of delivery of the active agent to the substrate. For active agents that are lipophilic drugs, such as ketoconazole, the solids content can be adjusted to more effectively saturate the substrate with the active agent upon application of the O/W emulsion. On the other hand, for active agents that are hydrophilic drugs, such as niacinamide and hydrogen peroxide, the amount of water can be adjusted to more effectively saturate the substrate with the active agent upon application of the O/W emulsion. The steps involved in providing the O/W emulsion relative to the mechanical inversion are additionally described in U.S. Provisional Patent Application No. 60/489,405, entitled "A Mechanical Inversion Process for Making Silicone Oil-in-Water Emulsions" and filed on Jul. 23, 2003, the disclosure of which is hereby incorporated by reference in its entirety.

As alluded to above, the active agent can be incorporated during the steps that are undertaken to provide the O/W emulsion. More specifically, the active agent may be incorporated into the O/W emulsion by incorporating the active agent into the homogenous oil phase during the providing of the O/W emulsion. Alternatively, the active agent may be incorporated into the O/W emulsion by incorporating the active agent along with the step of adding the water to for the W/O emulsion containing the continuous phase and the dispersed phase. That is, the active agent can be incorporated along with water. The O/W emulsion can contain other additives including, but not limited to, biocides, thickening agents (as described above), freeze-thaw stabilizers and electrically-conductive additives, such as an ionic species, to make a conductive O/W emulsion that can be used as electrodes in electrophoretic applications.

The method of delivering the active agent to the substrate further includes the step of applying the O/W emulsion to the substrate to deliver the active agent to the substrate. Upon application of the O/W emulsion, which contains the active agent, and upon exposure of the substrate to air, the water leaves the O/W emulsion and a film is formed on the substrate. The film contains the active agent. It is to be understood that exposing the substrate to air can essentially be instantaneous. There is no requirement that the substrate be exposed to air for prolonged periods of time. Instead, exposing the substrate to air can occur simultaneously as some of the O/W emulsion is being applied to the substrate.

Following application of the O/W emulsion to the substrate, it is believed that, as the water leaves and the O/W emulsion dries, the O/W emulsion does not coalesce. Instead, the film includes a condensed structural network on the substrate. It is believed that this condensed structural network has active agent that is dispersed throughout discrete packets of the silicone component. Furthermore, if utilized, the dispersing agent, which preferably encapsulates the active agent, functions to keep the discrete packets of the silicone component spaced thereby establishing and maintaining tortuous channels throughout the condensed structural network. These channels provide an avenue for delivery of the active agent to the substrate. It is also believed that some amount of water is retained in these channels due to hydrogen bonding that results from functional groups associated with the dispersing agent, e.g. an ethoxy group of a surfactant functioning as the dispersing agent.

In embodiments where the substrate is skin, the O/W emulsion is applied to the skin to deliver the active agent to the skin. It is to be appreciated that the skin does not have to be damaged or wounded. Instead, the controlled-release composition can be applied to skin that is intact. The O/W emulsion may be applied, i.e., rubbed or coated, directly onto the skin. Alternatively, the O/W emulsion may be deposited on a transdermal patch prior to application of the O/W emulsion to the substrate, i.e., to the skin. In this alternative scenario, the O/W emulsion is a hydrogel and the step of applying the O/W emulsion to the substrate is further defined as applying the transdermal patch to the skin to deliver the active agent to the skin.

The controlled-release composition according to this invention is capable of delivering performance properties such as controlled tack, controlled lubrication, water resistance, and barrier properties. This controlled-release composition has substantivity to the skin and other substrates, such as teeth. The significant substantivity of the composition is particularly advantageous when a controlled rate of delivery of the active agent is required over an extended period of time. Simply stated, the controlled-release composition is topically applied to the substrate where the film remains over the extended period of time. When the substrate is skin, the substantivity is important due to the presence of certain body oils and especially upon application to hairy skin. The composition also has substantivity to wet substrates such as teeth.

Examples 1-6

The following examples illustrating the formation of the controlled-release composition, as presented herein, are intended to illustrate and not to limit the invention. All references are to parts by weight unless otherwise indicated.

TABLE 1

| Example | Active Agent | Amt. Of Water | Amt. Of O/W Emulsion | Amt. Of Active Agent | Amt. Of Dispersing Agent No. 1 | Amt. Of Dispersing Agent No. 2 |
| --- | --- | --- | --- | --- | --- | --- |
| 1 | Niacinamide | 10 | 85 | 5 | 0 | 0 |
| 2 | Niacinamide | 10 | 80 | 5 | 5 | 0 |
| 3 | Niacinamide | 10 | 80 | 5 | 0 | 5 |
| 4 | Ketoconazole | 10 | 85 | 5 | 0 | 0 |
| 5 | Ketoconazole | 10 | 80 | 5 | 5 | 0 |
| 6 | Ketoconazole | 10 | 80 | 5 | 0 | 5 |

For Examples 1-6, the O/W emulsion was prepared as described above.

Dispersing Agent No. 1 is DC 193 Fluid which is a silicone glycol copolymer commercially available from Dow Corning, Midland, Mich. Dispersing Agent No. 2 is Emulsifier 10 which is a mixture of alkylmethyl siloxane copolyol, isostearyl alcohol, and 1-dodecene which is also commercially available from Dow Corning. In Examples 1-6, Dispersing Agent Nos. 1 and 2 were separately added to the active agent, either the niacinamide or ketoconazole, to form a dispersion and the resulting dispersion was then incorporated into the O/W emulsion.

Examples 7-15

Figure 2:
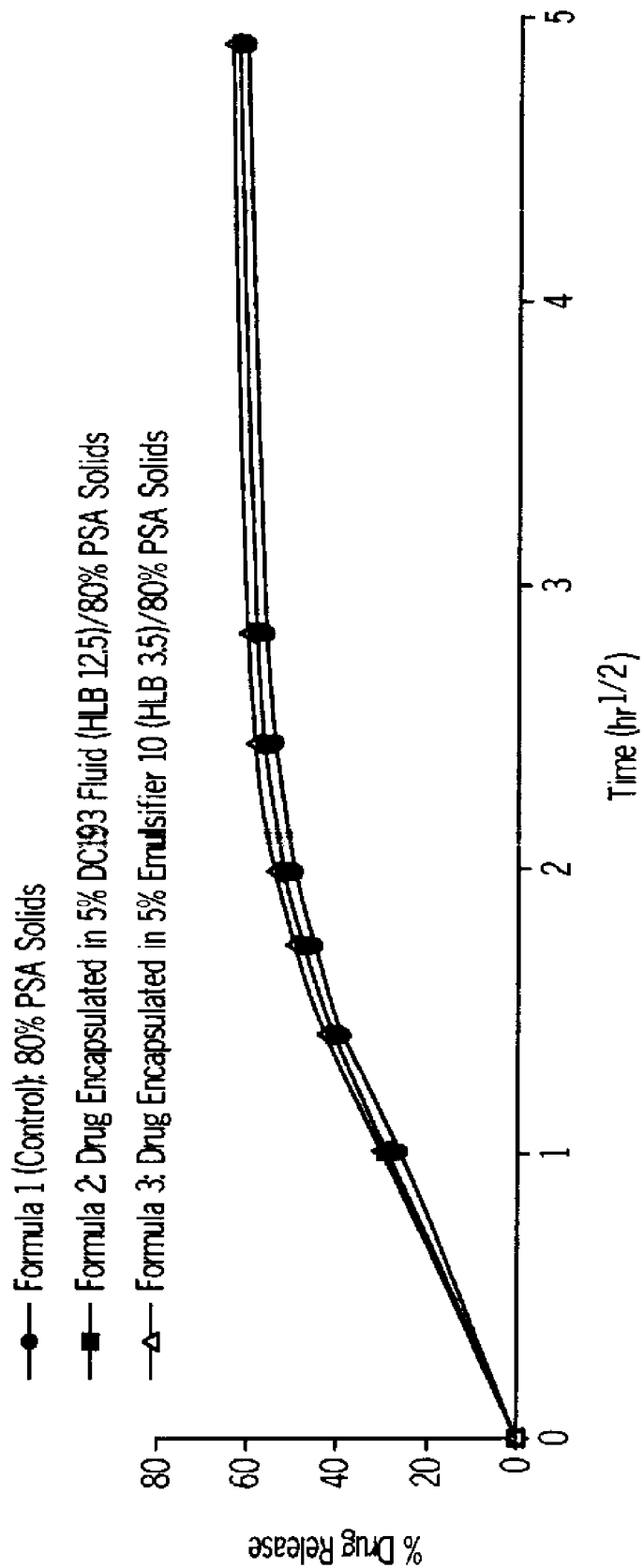
FIG. 2 is a graph showing the High Shear PSA O/W Emulsion: 6 Months RT 5% w/w Niacinamide.
Figure 3:
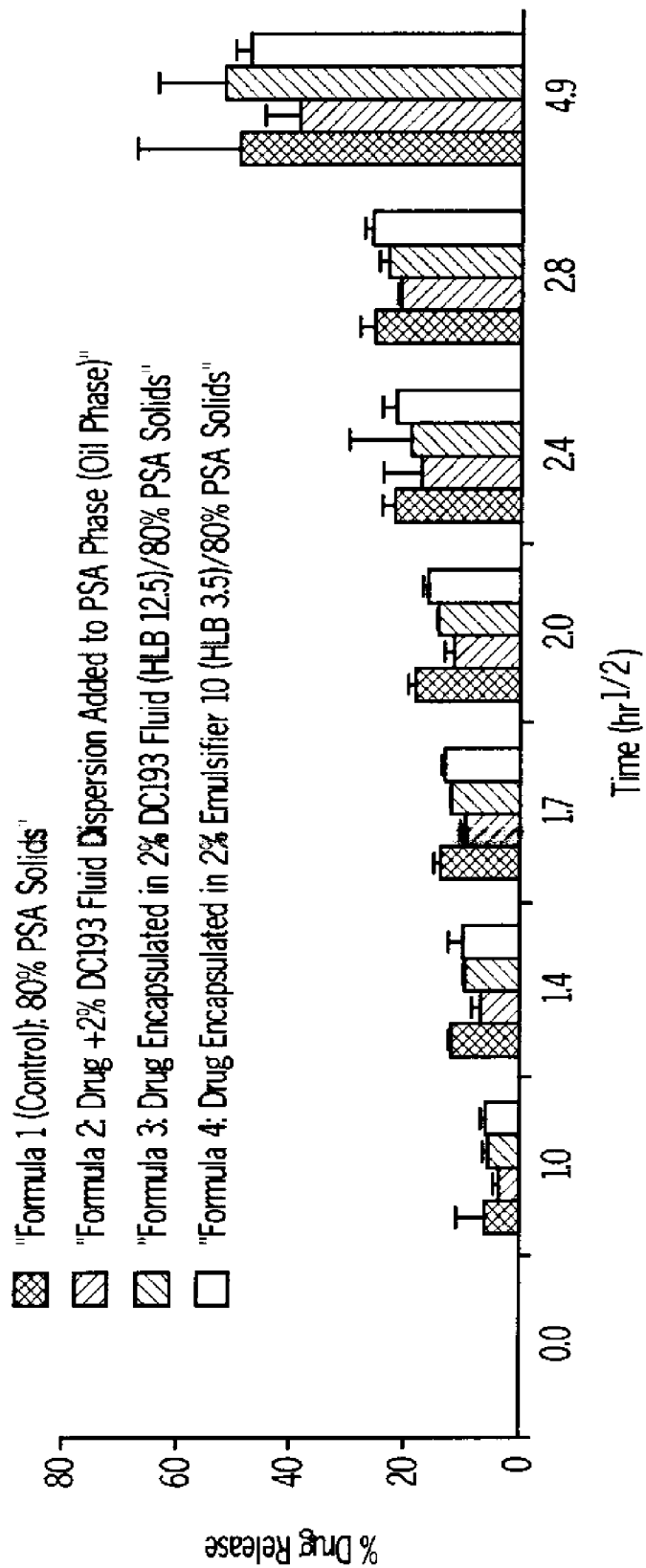
FIG. 3 is a graph showing the High Shear PSA O/W Emulsion: 2% w/w Ketoconazole.

For Examples 7-15, a drug, i.e., active agent, release study was conducted to evaluate the controlled release of topical niacinamide as the active agent over time. Determination of active agent dissolution rate was conducted in Franz static diffusion cells. The controlled-release compositions for Examples 7-15 were prepared according to the high shear, mechanical inversion process described above and were tested in triplicate. The Franz cells have a defined receiving volume. The controlled-release compositions were weighed on Hill Top Chambers® to provide constant thickness and surface area. A <3500 daltons dialysis membrane was placed on top of each Franz static diffusion cell to support the controlled-release composition. The receptor fluid was normal saline. Samples were taken from the receptor fluid at 1, 2, 3, 4, 6, 8, and 24 hours. Samples were analyzed by UV at 261 nm. Calibration curves yielded r values >0.999. The results for Examples 7-15 are disclosed below. Examples 7-9 correlate to Formulas 1-3, respectfully, in FIG. 1, Examples 10-12 correlate to Formulas 1-3, respectively in FIG. 2, and Examples 13-15 correlate to Formulas 1-3, respectively, in FIG. 3.

Obviously, many modifications and variations of the present invention are possible in view of the above teachings. The embodiments of the invention specifically illustrated herein are exemplary only and not intended as limitations on scope except as defined in the appended claims. Further, the invention may be practiced otherwise than as specifically described within the scope of the appended claims.

What is claimed is:

1. A controlled-release composition for topical application to a substrate, said composition comprising:
   an oil-in-water emulsion that is substantially free of lipophilic solvent and formed by mechanical inversion of a water-in-oil emulsion comprising a silicone component, a surfactant, and water; and
   an active agent incorporated into said oil-in-water emulsion.

2. A controlled-release composition as set forth in claim 1 further comprising a dispersing agent for dispersing said active agent.

3. A controlled-release composition as set forth in claim 2 wherein said dispersing agent comprises a silicone-based surfactant different from said surfactant.

4. A controlled-release composition as set forth in claim 2 wherein said dispersing agent is selected from the group of nonionic surfactants, anionic surfactants, ethers, esters, glycols, and combinations thereof.

5. A controlled-release composition as set forth in claim 2 wherein said active agent is in powder form or crystalline form.

6. A controlled-release composition as set forth in claim 5 wherein said dispersing agent encapsulates said active agent.

7. A controlled-release composition as set forth in claim 1 wherein said active agent is in liquid or viscous form.

8. A controlled-release composition as set forth in claim 1 wherein said silicone component is selected from the group consisting of a silicone gum, a silicone rubber, a silicone elastomer, a silicone resin, high molecular weight silicones, and mixtures thereof.

9. A controlled-release composition as set forth in claim 1 wherein said silicone component comprises a pressure sensitive adhesive.

10. A controlled-release composition as set forth in claim 9 wherein said pressure sensitive adhesive comprises the reaction product of;
a hydroxy endblocked polydimethylsiloxane polymer, and
a hydroxy functional silicate resin.

11. A controlled-release composition as set forth in claim 10 wherein said hydroxy functional silicate resin is further defined as a trimethylsiloxy and hydroxy endblocked silicate resin.

12. A controlled-release composition as set forth in claim 1 wherein said active agent comprises a lipophilic drug.

13. A controlled-release composition as set forth in claim 1 wherein said active agent comprises a hydrophilic drug.

14. A controlled-release composition as set forth in claim 1 wherein said silicone component and said surfactant are in a homogenous oil phase.

15. A controlled-release composition as set forth in claim 1 further comprising an excipient.

16. A controlled-release composition as set forth in claim 15 wherein said excipient comprises a thickening agent for stabilizing said active agent and said oil-in-water emulsion.

17. A controlled-release composition as set forth in claim 16 wherein said thickening agent comprises at least one of polyacrylic acids, cellulose derivatives, polyvinyl alcohol, polyvinylpyrrolidone, polysaccharides, acrylamide copolymers, biological polymers and derivatives, butylene copolymers, carbohydrates, carbomers, hydrophilic colloids and derivatives including salts and gums, polyacrylates and acrylate copolymers, synthetic polymers including salts, silica, calcium carbonates which can be untreated or treated with stearate or stearic acid, reinforcing silicas such as fumed silicas, precipitated silicas, and hydrophobed silicas, crushed quartz, ground quartz, alumina, aluminum hydroxide, titanium dioxide, diatomaceous earth, iron oxide, carbon black, and graphite, and resinous materials including silicone and organics.

18. A controlled-release composition as set forth in claim 1 wherein the oil-in-water emulsion has a solids content of from 25 to 85 parts by weight based on 100 parts by weight of the oil-in-water emulsion.

19. A method of delivering an active agent to a substrate, said method comprising the steps of:
providing an oil-in-water emulsion that is substantially free of lipophilic solvent and comprises a silicone-component, a surfactant, and water; and
incorporating the active agent into the oil-in-water emulsion for delivery of the active agent to the substrate upon application of the oil-in-water emulsion to the substrate.

20. A method as set forth in claim 19 further comprising the step of encapsulating the active agent in a dispersing agent prior to incorporation of the active agent into the oil-in-water emulsion.

21. A method as set forth in claim 20 wherein the dispersing agent allows a controlled rate of delivery of the active agent to the substrate.

22. A method as set forth in claim 20 further comprising the step of applying the oil-in-water emulsion to the substrate to deliver the encapsulated active agent to the substrate.

23. A method as set forth in claim 19 further comprising the step of combining the active agent with a dispersing agent to form a dispersion prior to incorporation of the active agent into the oil-in-water emulsion.

24. A method as set forth in claim 19 wherein the step of providing the oil-in-water emulsion comprises the step of forming a homogeneous oil phase containing the silicone-component.

25. A method as set forth in claim 24 wherein the step of incorporating the active agent into the oil-in-water emulsion is further defined as incorporating the active agent into the homogenous oil phase.

26. A method as set forth in claim 19 wherein the step of incorporating the active agent into the oil-in-water emulsion is further defined as incorporating the active agent along with water.

27. A method as set forth in claim 19 wherein the step of providing the oil-in-water emulsion further comprises the step of mechanically-inverting the water-in-oil emulsion into the oil-in-water emulsion.

28. A method as set forth in claim 19 wherein the silicone component is selected from the group consisting of a silicone gum, a silicone rubber, a silicone elastomer, a silicone resin, high molecular weight silicones, and mixtures thereof.

29. A method as set forth in claim 19 wherein the silicone component comprises a pressure sensitive adhesive.

30. A method as set forth in claim 19 wherein the active agent comprises a lipophilic drug.

31. A method as set forth in claim 19 wherein the active agent comprises a hydrophilic drug.

32. A method as set forth in claim 19 further comprising the step of applying the oil-in-water emulsion to the substrate to deliver the active agent to the substrate.

33. A method as set forth in claim 32 wherein the substrate is skin and the step of applying the oil-in-water emulsion to the substrate is further defined as applying the oil-in-water emulsion to the skin to deliver the active agent to the skin.

34. A method as set forth in claim 32 further comprising the step of depositing the oil-in-water emulsion on a transdermal patch prior to applying the oil-in-water emulsion to the substrate.

35. A method as set forth in claim 34 wherein the substrate is skin and the step of applying the oil-in-water emulsion to the substrate is further defined as applying the transdermal patch to the skin to deliver the active agent to the skin.

36. A method as set forth in claim 19 further comprising the step of incorporating an excipient into the oil-in-water emulsion.

37. A method as set forth in claim 19 wherein the substrate comprises one of a biological surface, human body tissue, and animal body tissue.

38. A method as set forth in claim 19 wherein the substrate comprises flora.

39. A method as set forth in claim 32 further comprising the step of exposing the substrate to air such that the water leaves the oil-in-water emulsion and a film is formed on the substrate.

40. A method as set forth in claim 39 wherein the substrate is skin and the film that is formed functions as at least one of a topical drug delivery system, a masking system for skin protection in dermal treatments, a wound dressing or bandage for wounds, burns, acute and chronic wounds, a skin sealant, a skin protective film, a scar treatment, an exfoliation product, an antimicrobial agent such as silver ions, a hair remover products, a deodorizing film, an antiperspirant active and fragrance delivery system, an anti-wrinkle patch, a moisturizing mask, and wherein the film has benefits in topical therapies, wound care, surgical closure, scar care, underarm care, foot care, body and face skin care, cosmetics, make-up and foundations, insect repellents.

41. A method as set forth in claim 39 further comprising the step of transferring the film to a second substrate.

* * * * *